US010016552B2

(12) United States Patent
Koch (10) Patent No.: US 10,016,552 B2
(45) Date of Patent: Jul. 10, 2018

(54) METHOD OF ULTRASONIC DEGASSING OF LIQUIDS FOR DIALYSIS (71) Applicant: Fresenius Medical Care Deutschland GmbH, Bad Homburg (DE)

(72) Inventor: Michael Koch, Gerolzhofen (DE)

(73) Assignee: FRESENIUS MEDICAL CARE DEUTSCHLAND, Bad Homburg (DE)

( * ) Notice: Subject to any disclaimer, the term of this patent is extended or adjusted under 35 U.S.C. 154(b) by 294 days.

(21) Appl. No.: 14/784,118

(22) PCT Filed: Mar. 27, 2014

(86) PCT No.: PCT/EP2014/056155
§ 371 (c)(1),
(2) Date: Oct. 13, 2015

(87) PCT Pub. No.: WO2014/166748
PCT Pub. Date: Oct. 16, 2014

(65) Prior Publication Data
US 2016/0067398 A1 Mar. 10, 2016

(30) Foreign Application Priority Data
Apr. 11, 2013 (DE) .................. 10 2013 006 667

(51) Int. Cl.
B01D 19/00 (2006.01)
A61M 1/16 (2006.01)
C02F 1/20 (2006.01)
A61M 1/36 (2006.01)
C02F 1/36 (2006.01)
C02F 1/44 (2006.01)
C02F 103/02 (2006.01)

(52) U.S. Cl.
CPC .......... *A61M 1/1658* (2013.01); *A61M 1/363* (2014.02); *B01D 19/0063* (2013.01); *B01D 19/0078* (2013.01); *C02F 1/20* (2013.01); *C02F 1/36* (2013.01); *A61M 2205/123* (2013.01); *C02F 1/44* (2013.01); *C02F 2103/026* (2013.01)

(58) Field of Classification Search
None
See application file for complete search history.

(56) References Cited

U.S. PATENT DOCUMENTS

| 5,022,899 A | 6/1991 | Hohlfeld et al. |
| 2002/0091350 A1* | 7/2002 | Belson ............... A61M 1/16 604/5.04 |
| 2007/0045188 A1 | 3/2007 | Blanton |

(Continued)

FOREIGN PATENT DOCUMENTS

| DE | 4020840 | 1/1992 |
| EP | 1820550 | 8/2007 |
| JP | 2002018202 | 1/2002 |

(Continued)

*Primary Examiner* — Amber R Orlando
*Assistant Examiner* — Phillip Y Shao
(74) *Attorney, Agent, or Firm* — Jacobson Holman, PLLC (57) ABSTRACT A device for degassing liquids, in particular liquids used in dialysis, has a degassing unit that includes an ultrasonic unit. Liquids to be degassed are treated in the degassing unit by ultrasound from the ultrasonic unit. Degassed liquids are discharged from the degassing unit through a hollow channel in the ultrasonic unit, and are available for further use.

15 Claims, 3 Drawing Sheets

(56) References Cited

U.S. PATENT DOCUMENTS

2009/0084718 A1* 4/2009 Prisco ................. A61M 1/1658
                                                                210/151
2010/0152625 A1    6/2010 Milo

FOREIGN PATENT DOCUMENTS

| WO | WO 97/20612 | 6/1997 |
| WO | WO 01/41655 | 6/2001 |

* cited by examiner

METHOD OF ULTRASONIC DEGASSING OF LIQUIDS FOR DIALYSIS

BACKGROUND OF THE INVENTION

1. Field of the Invention

The subject matter of the present invention is a device and a method for ultrasonic degassing of liquids that are used in dialysis.

2. Description of Related Art

During dialysis, the blood of patients with kidney damage is brought in contact with an exchange fluid through a dialysis membrane. Such dialysis fluids remove from the patients blood the toxic metabolites that can no longer be excreted by the patient himself, so they can then be discarded. Dialysis thus has a purification effect on the blood treated.

In hemodialysis, a mass exchange takes place on an artificial membrane in an extracorporeal blood circulation, whereas in peritoneal dialysis, the patients peritoneum is used as an exchange membrane.

In addition, treatment fluids are also infused directly into the blood to be treated in dialysis therapy and other therapies of extracorporeal blood treatment.

From a medical standpoint, it is inadmissible for any gas inclusions that might occur to be infused with the treatment fluid, and this should absolutely be avoided at the risk of the patient's life.

Gas inclusions in the treatment fluid can cause a medically hazardous situation for the patient in a dialysis treatment in which the treatment fluid is in mass exchange contact with the blood separately through the membrane.

Dialysis machines that are used to perform extracorporeal blood dialysis or peritoneal dialysis are characterized by a complex system of control circuits and measurement devices, control devices and alarm devices. Any gas inclusions in the treatment fluids are detected continuously by a corresponding monitoring system and are announced by alarm signals. Pressure measurement equipment or balancing equipment of such dialysis machines would otherwise create defective outputs, so that a patient's treatment would be disturbed or could not be performed.

In areas where the dialysis fluid is exposed to a vacuum due to the delivery pump equipment, a spontaneous separation of gas in the form of trapped gas bubbles has been observed when the gas load in the treatment fluid became too high. Such situations occur in particular downstream from throttle points in the dialysis fluid branch of the extracorporeal blood circulation. Such throttle points include, for example, constrictions after which there is a significant drop in pressure, in particular when the delivery pump is also situated downstream from the throttle location.

In dialysis methods of extracorporeal blood treatment, the dialysis filter is one such throttle point. Thus, on the whole, there is always a need for the treatment fluids to be carefully degassed when the treatment fluids come in contact with the blood to be treated.

In addition, the degassing of a treatment fluid induced by the thermodynamic gas-solution equilibrium when there is an increase in temperature becomes a source for the occurrence of gas inclusions. At elevated temperatures, the solution capacity of gases in an aqueous solution is reduced. A treatment fluid prepared at room temperature and then heated to the physiological temperature of the patient necessarily tends to release dissolved gases in the form of a gas.

In addition, a gas load may also occur due to microbubbles which are separated from the treatment fluid only slowly. In particular such a burden can occur when the treatment fluids are prepared from dry, pasty or syrupy concentrates through dilution and turbulence with water. The concentrates themselves may already have microscopic gas inclusions which are absorbed into the treatment fluid on dilution with water.

Therefore, with dialysis machines, there is always a need for degassing treatment fluids. In the state of the art, the degassing of treatment fluids in dialysis machines is described as follows:

DE 40 20 840 A1 describes a device for degassing a fluid by applying heat. The fluid to be degassed is heated to a temperature near the boiling point and then is cooled again on a hollow-fiber membrane module, which serves as a heat exchanger.

JP 2002018202 describes a degassing device for portable dialysis machines. A separation of fluid and gas inclusions is accomplished in a chamber by applying ultrasound. The gas inclusions thereby separated can be discharged through the channels in the chamber wall.

It is also known in the state of the art that degassing may be accomplished by applying a reduced pressure. The fluid to be degassed is subjected to a vacuum in a chamber of a degassing unit. The fluid is discharged by a pump and is separated from the gas inclusions in a second chamber. The fluid must be removed from the degassing unit by a pump mechanism. In passing through the pump mechanism, a portion of the separated gases becomes dissolved again in the liquid. According to this principle, degassing can never proceed as completely as would be allowed by application of a vacuum per se.

The principle of redissolving gas in the liquid in the degassing units of dialysis machines is a general problem which makes degassing an inefficient operation. This disadvantage is reflected in part in the equipment design of the degassing units. The degassing unit must be designed to be larger accordingly, so that redissolving phenomena which are unavoidable can be compensated by a greater degassing performance of the system. An increase in efficiency thus not only achieves energy savings during operation of the degassing unit but then the entire degassing unit may also be designed to be smaller and the equipment to be less expensive.

Current developments involving dialysis machines are increasingly going in the direction of building up the extracorporeal blood circulation from disposable articles. The hope was for this development to permit faster handling for the clinic personnel, in particular by reducing setup and breakdown times on the dialysis machines.

Subsequently, the trend in developments has been for the disposable articles to constitute highly integrated systems having ever increasing numbers of functionalities. In the best case, according to these efforts, the disposable article is designed so that it already contains all the necessary functionalities for dialysis.

In this way, disinfection and rinsing operations on the treatment device can be largely omitted. This makes the treatment device less expensive and more universally usable.

There are of course limits to the structural technical possibilities of disposable articles. The design size, weight and material of a disposable article are limited with regard to handling, price and disposal.

There is therefore a need for providing a degassing unit for liquids which are relevant in kidney dialysis or in an extracorporeal blood treatment in comparison with the state of the art, such that this degassing unit has a low equipment complexity and is thus inexpensive to operate and manufacture.

SUMMARY OF THE INVENTION

One object of the present invention is therefore to develop a degassing apparatus that does not require the conventional degassing components of applying a vacuum and applying heat and can be accommodated on a disposable article.

Another object has been to make the degassing technology as efficient as possible, so that a good degassing performance can be achieved despite corresponding miniaturization.

This object is achieved by the features of the invention described herein. Other features of the invention that are preferred specific embodiments thereof are also described herein.

According to this invention, a device for degassing a treatment fluid, which may also be referred to as a degassing unit, comprises a container holding the treatment fluid that is to be degassed for the dialysis. This container also holds an ultrasonic sonotrode, which is provided for transferring the ultrasonic energy to the fluid. In the present context, the sonotrode should be understood to be a combination of an oscillator and a resonator. The oscillator generates or transmits oscillations, which are introduced as an ultrasonic signal into the fluid to be degassed. The resonator is coupled to the oscillator in such a way that it transmits the oscillations of the oscillator to the fluid.

The resonator has fluid flowing around it or is immersed in the fluid, which is in a container. By activation of the resonator, degassing of the treatment fluid is induced. The resonator is also characterized in that it contains an internal hollow channel through which the gas/liquid mixture that is to be separated by ultrasound can be discharged out of the container.

Through this arrangement, the ultrasound thus generated is introduced via the resonator directly into the liquid. The degassing efficiency is the greatest in the immediate vicinity of the resonator. The degassed mixture of liquid and separated gas can be discharged directly from the degassing unit via the hollow channel incorporated into the resonator, so that backmixing of the gas can be prevented. Ultimately an efficiency optimum which makes it possible to keep the component size small is achieved through degassing and suction filtration induced simultaneously. The small component size makes it possible to accommodate the degassing unit on a disposable article, also referred to simply as a disposable, for dialysis treatments or for an extracorporeal blood treatment.

The container may be a chamber in a dialysis machine prepared to receive fluids or a disposable article for a dialysis treatment. If degassing is performed continuously on the liquid flowing through the machine in one embodiment, the chamber may have a volume of 1 mL to 500 mL. Alternatively, volumes of 5 mL to 350 mL or 5 mL to 250 mL may also be provided for the degassing unit.

In cases in which the degassing unit is part of a disposable article, an integrated cassette module for the extracorporeal blood treatment or peritoneal dialysis, smaller volumes are to be provided for the degassing unit accordingly. In this case, chambers with a volume of 1 mL to 50 mL may be considered.

The size of the chambers also depends on the flow principle with which the fluids to be degassed are passed through the disposable article. In the case of a discontinuous flow, larger volumes are to be provided for the chamber accordingly, whereas smaller chamber volumes are to be used with a continuous flow principle.

In addition, the performance of the ultrasonic oscillator is of crucial importance, with which flow rate and optionally with which flow principle the fluid to be degassed can be transported through the degassing unit. For the applications of degassing of fluids for dialysis that may be considered, oscillator power outputs of 50 W to 1000 W have proven to be advantageous.

Ultrasonic sonotrodes for treatment of fluids are known in general. The sonotrodes have a rod-shaped or tip-shaped geometry, which is understood to mean that the cross-sectional diameter of the sonotrode is smaller than the longitudinal extent.

In the inventive design of the resonator, which is designed as a tip, this yields the advantage that the greatest power input of the resonator oscillation into the liquid to be degassed takes place at the tip of the resonator. A mixture of degassed liquid and separated gas can be discharged jointly through the discharge channel situated on the inside in the resonator. Since the mixture need not be discharged through a separate pump, there is no risk of backmixing of the separated gas with the liquid in a discharging pump mechanism.

According to the principle of the oscillator and the resonator, the mechanical waves generated by the oscillator propagate longitudinally in the direction of extent of the resonator. At the tip of the resonator, the mechanical actuation is transferred to the surrounding liquid. If the sonotrode tip tapers conically or in a hyperboloid shape, there is additionally an increase in the mechanical energy density at the tip. In one embodiment, in which the oscillator is designed as an elongated tip, the power input into the liquid to be degassed is therefore the greatest at a given frequency and power of the sonotrode.

A resonator is usually coupled to an oscillator, which generates piezoelectrically generated mechanical oscillations or transmits such oscillations from a separate oscillation generator. A piezo element is induced to oscillate by applying an electric voltage according to the piezoelectric effect. Oscillation frequencies above 20,000 Hertz (20 kHz) are generally used, so they are not perceptible to the human ear. For the present invention, a resonator is operated at frequencies above 20 kHz, frequencies of 25 to 40 kHz in particular being advantageous.

The oscillator and resonator may be integrated into a disposable article within the container, which may also be referred to as a degassing unit. Such disposable articles may be made of a flexurally rigid injection molding material, e.g., polypropylene. The degassing unit may take up a part on the disposable article. The degassing unit may have electrical contacts on the disposable article, which are connected to a dialysis machine during the dialysis treatment and which transmit the required electrical energy for the sonotrode.

The term "treatment fluid" in conjunction with this invention is understood to refer to all liquids which are required for treatment of the dialysis-dependent patient during a treatment. This is understood in particular to include dialysis fluids used in hemodialysis and peritoneal dialysis. In addition, substitution fluids and infusion fluids are also included. This also includes rinsing fluids with which the disposable articles are prerinsed before the treatment and filled in the absence of air.

Dialysis is understood to refer to all treatment methods associated with purification of blood in which the blood is purified through a membrane. The following may be mentioned as examples, although this list is not exhaustive: dialysis methods, hemofiltration methods, hemodiafiltration methods, plasmapheresis methods and peritoneal dialysis methods.

In general, vacuoles on a microscopic scale may be formed in the ultrasonic treatment of liquids. When these vacuoles collapse, sound waves in the audible range are emitted, causing interference for the environment which is perceived as cavitation noise. In the therapeutic field in particular such noise production is to be avoided or shielded with sound suppression measures. It has been found that unpleasant cavitation sounds can be prevented by a hyperbolic oscillator shape. In one embodiment, it is therefore provided that the oscillator is designed like a hyperboloid. The side faces then have a hyperbolic contour in the longitudinal cross section.

Another advantage of ultrasonic degassing is that it is possible to work on open degassing units. This is understood to mean that the degassing unit may be in pressure equalization with other liquid-carrying sections. Degassing units in vacuum degassing require closed chambers, for example, so there is only the possibility of draining the gas/liquid mixture out of the degassing unit by means of pumps. One disadvantage here is that the gas in the gas/liquid mixture is partially dissolved back into the liquid within the pump mechanism, which makes the degassing process inefficient.

In the present invention, the treated gas/liquid mixture may be discharged from the degassing unit by applying a slight excess pressure in the degassing unit. Excess pressure can build up due to the incoming fluid in a continuous flow principle. Alternatively, a slight excess gas pressure may be established in the gas space above the liquid by using pump means.

In this case, the degassing unit is connected to an inlet channel through which incoming fluid is conveyed into the degassing unit. The pump means may comprise diaphragm pumps, for example. Alternatively, the excess pressure may also be supplied by a pressure reservoir. In addition, the degassing unit has a connection through which a gas can be supplied to the degassing unit. In addition, the gas/liquid mixture can be discharged through the hollow channel in the resonator as described above.

It is sufficient if the excess pressure is set a few mbar higher than atmospheric pressure. The excess pressure may be from 5 to 200 mbar up to 50 mbar or up to 100 mbar, depending on the operating status of the degassing unit.

It is also provided that the degassing mixture, which is discharged from the degassing unit through the hollow channel of the oscillator, is sent to a second container, which may be designated as a separation chamber. Separation chambers for separating gases and liquids are known in the state of the art. Such separation chambers in which the gas/liquid mixture is introduced tangentially into a separation chamber having a round cross section are known in the state of the art. Such separation chambers in which the gas/liquid mixture is introduced tangentially into a separation chamber having a round cross section are preferred.

It is not necessary for the resonator and oscillator to be fixedly connected to the degassing unit. An embodiment in which the resonator and oscillator are designed as floats may be advantageous. The oscillator as a float will always float on the surface of the liquid and will also be immersed in the liquid even with variable liquid levels. Alternatively, it is possible to provide that the float is connected to the degassing unit via a guide but is freely movable with the variable liquid horizon within the guide. This therefore yields the advantage that the float always works at an optimal depth of penetration and the degassing can proceed effectively regardless of the liquid level.

In one alternative embodiment, the degassing unit and the resonator are designed so that the resonator is immersed completely in the liquid. It is provided in particular that the hyperbolic body of the resonator is arranged so that the tip lies near the air/liquid or gas/liquid interface and the entire resonator is inside the liquid. The oscillator here need not be surrounded by the liquid completely or at all. In this context, it is important only that the resonator is in the greatest possible contact with the liquid to be degassed. The arrangement of the resonator, the degassing unit and the oscillator may appear so that the oscillator is installed as a part in the wall of the degassing unit. A liquid-tight and airtight connection between the wall of the degassing unit and the oscillator is established by means of seals. Sealing means for this are sufficiently well known to those skilled in the art.

The degassed mixture is advantageously removed through the hollow channel of the resonator, and partially formed gas bubbles at the tip are removed in the opposite direction. The gas bubbles rise up to the gas/liquid interface in accordance with their buoyancy. The degassed mixture is removed downward from the interface in accordance with the geometry of the resonator. In a step preceding the actual separation of liquid and gas, this facilitates a separation of the two media already in the degassing unit. The gas/liquid mixture discharged through the hollow channel of the resonator may be discharged by means of an applied excess pressure in the degassing unit or a vacuum that is set in the separation chamber which is arranged outside of the degassing unit. Excess pressure and reduced pressure here relate to the normal pressure of the ambient atmosphere.

According to this arrangement of resonator and degassing unit, a degassing valve is advantageously also mounted on the degassing chamber; gas already separated in the degassing unit when the excess pressure was applied can be discharged through this valve. In addition, with this arrangement, it is important to be sure that the liquid level does not drop below the level of the resonator tip because otherwise air would be discharged through the hollow channel of the resonator, which would have a negative effect on the separation process in the downstream separation chamber. It is therefore possible to provide that a corresponding sensor that can detect a liquid level is to be mounted inside or outside the degassing unit. The signal can be evaluated accordingly by a controller, e.g., a processor unit. For the case when the liquid level is too low in comparison with the level of the resonator tip, the degassing process or the discharge through the hollow channel is interrupted accordingly.

A further embodiment provides for an arrangement of a degassing unit on a disposable article, in particular a cassette module for processing physiological fluids, e.g., in dialysis or infusion. In this arrangement, it is provided that the resonator is also integrated into the degassing unit, but the oscillator is not. The resonator is thus arranged in the degassing unit in such a way that it is in contact with a film or some other flexible wall section. The film or the flexible wall section borders and seals the degassing unit on one side. The resonator, the adjacent film or the flexible wall section and the degassing unit are preferably made of plastic materials, so that use of the cassette module as a disposable article is economically feasible. Accordingly, vibration-resistant components such as the bordering film and the resonator in particular are made of vibration-resistant materials, in particular materials that are both vibration-resistant and inexpensive. "Vibration-resistant" in this context is understood to mean that the ultrasonic power experiences the least possible damping due to the vibration-transmitting components.

In addition, the resonator may be arranged as in the embodiments described previously. Depending on the construction condition of the cassette module or the type of liquid to be degassed, the resonator may be immersed entirely in the liquid volume to be degassed or may be immersed only into the liquid at the resonator tip as long as the arrangement is able to ensure that the resonator may be in contact with a film bordering the degassing unit or a flexible wall section over a certain area. In this arrangement, it is possible to provide the oscillator separately from the disposable article. A degassing process takes place when the cassette module and the degassing unit are brought into vibration-transmitting contact with the oscillator. The oscillator may be provided in a console of a machine that is provided for the respective treatment of the patient. In the context of the invention described here, such machines include dialysis machines or infusion machines, for example.

Technical details of arrangements of machine consoles and treatment cassette modules have been described frequently in the state of the art. It is provided in the present case that the console part of a treatment machine is prepared for receiving a treatment cassette module, and the oscillator is arranged in a part of the console, so that it can be in direct contact with the cassette module. In particular the geometry of the cassette and the console are such that the oscillator can be in contact with the vibration-resistant film or the vibration-transmitting flexible wall section of the degassing unit, so the vibrations can be transmitted to the resonator and thus into the interior of the degassing unit. This separation of the oscillator and the resonator makes it possible to implement ultrasonic degassing in a disposable article in an economically favorable manner.

The device for degassing liquids is also advantageously designed, so that it includes a processor, a sensor and a control circuit. A regulating mechanism is created by means of this equipment in particular, so the ultrasonic power can be adapted to variable circumstances during degassing. The ultrasonic generator and/or the oscillator is/are connected in particular to a processor, which is configured so that it determines a control value based on a damping value that has been determined, and the frequency of the sonotrode is varied so that the damping is minimized.

The ultrasonic generator is operated at its greatest efficiency when it is operated in resonance with the surrounding liquid medium and the adjacent wall of the degassing unit. The acoustic properties of the liquid medium may change, for example, due to the amount of separated gas (e.g., air bubbles in water) or a variable liquid level in the degassing unit. The frequency of the ultrasonic sonotrode must therefore be (slightly) tunable for operation in order to be able to adapt the "resonant frequency" anew to altered ambient parameters in order to work in the most efficient resonant state. The system can be regulated through a phase control loop, which is also known by the term "phase-locked loop" (PLL), for example, and is known in the state of the art.

In principle, such a circuit is a mixed signal application: the point in time of the rising signal level (obtained electronically from the current; the phase accuracy is important) is determined with a threshold trigger. Time differences in comparison with the setpoint value are converted to a frequency-variable signal. This creates a control loop, which in turn creates a constant adjustment.

The present invention also relates to a method for degassing a liquid. The method includes the steps of introducing a liquid into a degassing unit, immersing a resonator in the liquid, degassing the liquid by means of an ultrasonic treatment and separating the liquid from gases dissolved or dispersed therein and discharging the liquid and/or gas from the degassing unit.

This method is preferably used in degassing of liquids, which are used as the treatment liquid in the extracorporeal blood treatment, in particular dialysis.

For this method, it is provided that the ultrasonic generator is operated at a power of 50 to 1000 W. Preferred frequency ranges are between 20 and 40 kHz.

The liquid medium is separated from dissolved or dispersed gas inclusions by the applied sonic waves. This separation is accomplished via an oscillator on a resonator, which is immersed in the liquid.

The oscillator is designed to be elongated, e.g., rod-shaped, so that effective separation of liquid and gas takes place at the tip of the rod-shaped oscillator, where the sound wave power applied to the system is the greatest. This tip is preferably created with hyperbolically shaped outside surfaces. Cavitation noises in the medium being degassed can be minimized by this hyperbolic shape.

The degassing method according to the invention is also advantageously characterized in that the gas/liquid mixture (hereinafter referred to as a fluid mixture) obtained at the resonator tip is discharged through a hollow channel in the interior of the oscillator. The fluid mixture is conveyed through the hollow channel by means of an excess pressure applied in the degassing unit and is discharged into a second chamber, where the gas and liquid are separated. It is also possible to apply a vacuum in the separation chamber as a method equivalent to applying an excess pressure in the degassing chamber, so that the fluid mixture is drawn by suction from the degassing unit into the separation chamber.

Gas components and liquid components are separated from one another in the separation chamber, so that the liquid component can be removed as a degassed liquid through a discharge channel. Corresponding separation methods and chambers are customary in the state of the art, in particular with dialysis machines. Separation in particular is understood here to mean that liquid and gas constituents are separated into two separate phases. The dispersed mixture of gas and liquid formed initially in the degassing chamber is thus converted completely to two phases.

In addition, the liquid can be removed from the separation chamber and supplied as treatment liquid or as a component of a treatment liquid for the extracorporeal blood treatment.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
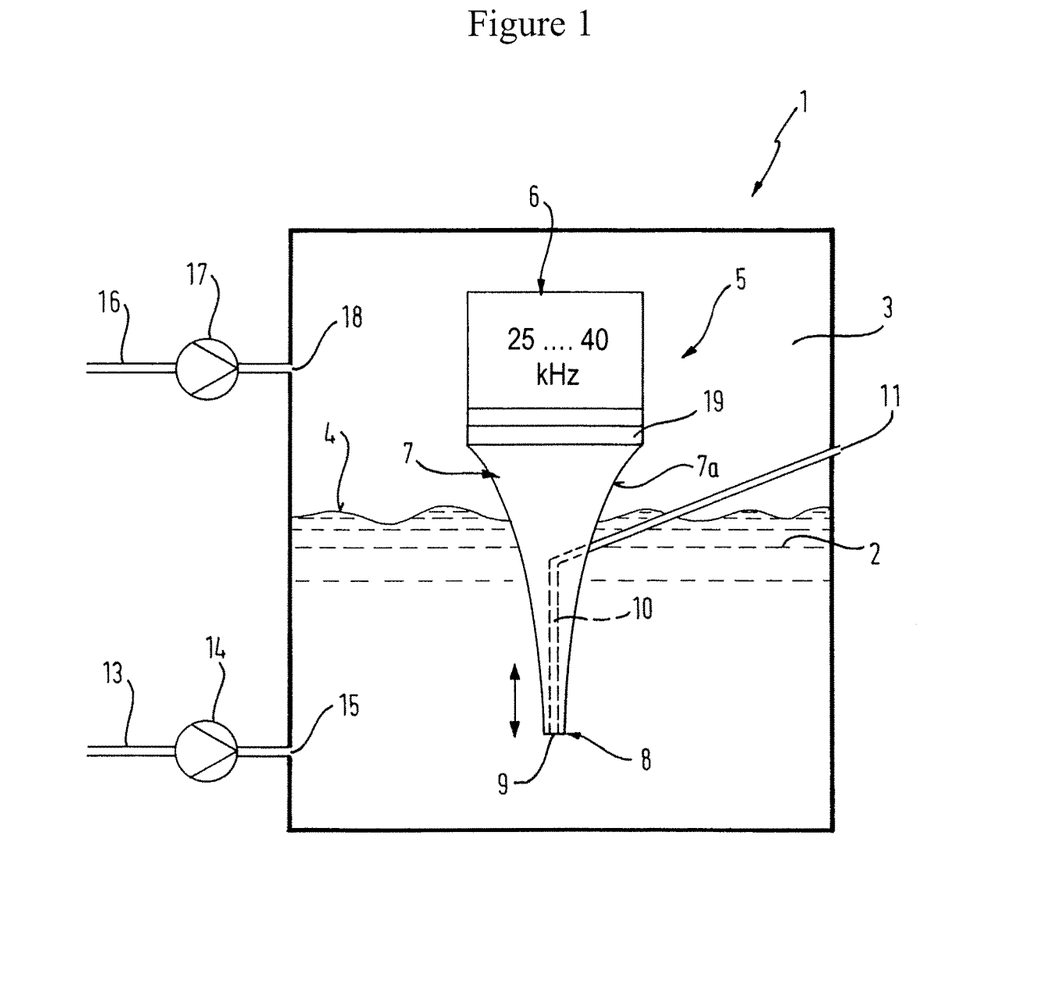
FIG. 1 depicts a degassing unit according to a first embodiment of the instant invention.

FIG. 1 shows a schematic diagram of the design of a degassing unit for degassing medical treatment liquids. The degassing unit 1 comprises a container in which a liquid 2, which is supplied for degassing, is stored. This liquid may be, for example, a dialysis solution or a component of a dialysis solution that is to be prepared. The liquid may flow through the container continuously in that liquid is resupplied to the container continuously through the opening 15, the pump 14 and the supply line 13. The container is only partially filled with the liquid. A gas space 3 is located above the liquid surface 4. The gas space 3 may usually be filled with air, in particular with sterile air, when medical treatment liquids are being degassed. Alternatively, additional gases, in particular nitrogen or inert gases may also be supplied for degassing. The gases may be supplied to the degassing unit through the supply line 17 by way of an opening 18 and a pump 17.

The degassing unit 1 additionally contains an ultrasonic unit 5, which is also referred to as a sonotrode, consisting of an oscillator 6 and a resonator 7. The resonator in the present example according to FIG. 1 is designed, so that the surface 7a has at least partially a hyperbolic curvature. In the elongated hyperbolic embodiment, the resonator has a tip 8, which is immersed in the liquid medium to be degassed. A hollow channel 10, which is shown with dotted lines in the figure and is in contact with the liquid medium 2 through the opening 9, is situated in the interior of the resonator. An ultrasonically treated gas/liquid mixture from the degassing unit 1 can be discharged through the opening 9, the hollow channel 10 and the opening 11 and can be received in another vessel (not shown) for separation of gas and liquid.

During the degassing process, the ultrasonic generator operates at a frequency of 25 to 40 kHz in the best case. The mechanical oscillation energy is input into the liquid medium 2 through the connection 19 of the resonator. The resonator essentially performs oscillations in the direction of the double arrow shown in FIG. 1. Since the input of mechanical energy is the greatest at the tip 8 of the resonator, the greatest degassing occurs here directly adjacent to the opening 9. The degassing therefore becomes especially efficient because the gas/liquid mixture that is separated can be discharged directly from the chamber, and any redissolving processes can thus be largely prevented. The discharge process is made possible here due to the buildup of excess pressure due to the pumps 14 or 17. FIG. 1 shows schematically the two pumps 14, 17 and the respective supply lines 13, 16. However, two pumps and supply lines are not necessarily essential for operation, so that it would also be possible to omit pump 17 and supply line 16. Pump 17 serves mainly to create the desired excess pressure in the degassing unit 1 by supplying a gas such as air to the degassing unit. The rate at which liquid degassed at the tip 8 is discharged from the degassing unit can be regulated via the excess pressure that is set.

In alternative embodiments, it is possible to omit the pump 17, supply channel 16 and opening 18. In such embodiments an excess pressure is established through the supplied liquid via the pump 14 and the liquid gas mixture is thereby discharged out of the chamber 1. The mixture is transferred to a second container for separation of gas and liquid (not shown in FIG. 1). The degassed liquid is removed selectively from the second container, which may also be referred to as the separation chamber, for further use in dialysis therapy.

Figure 2:
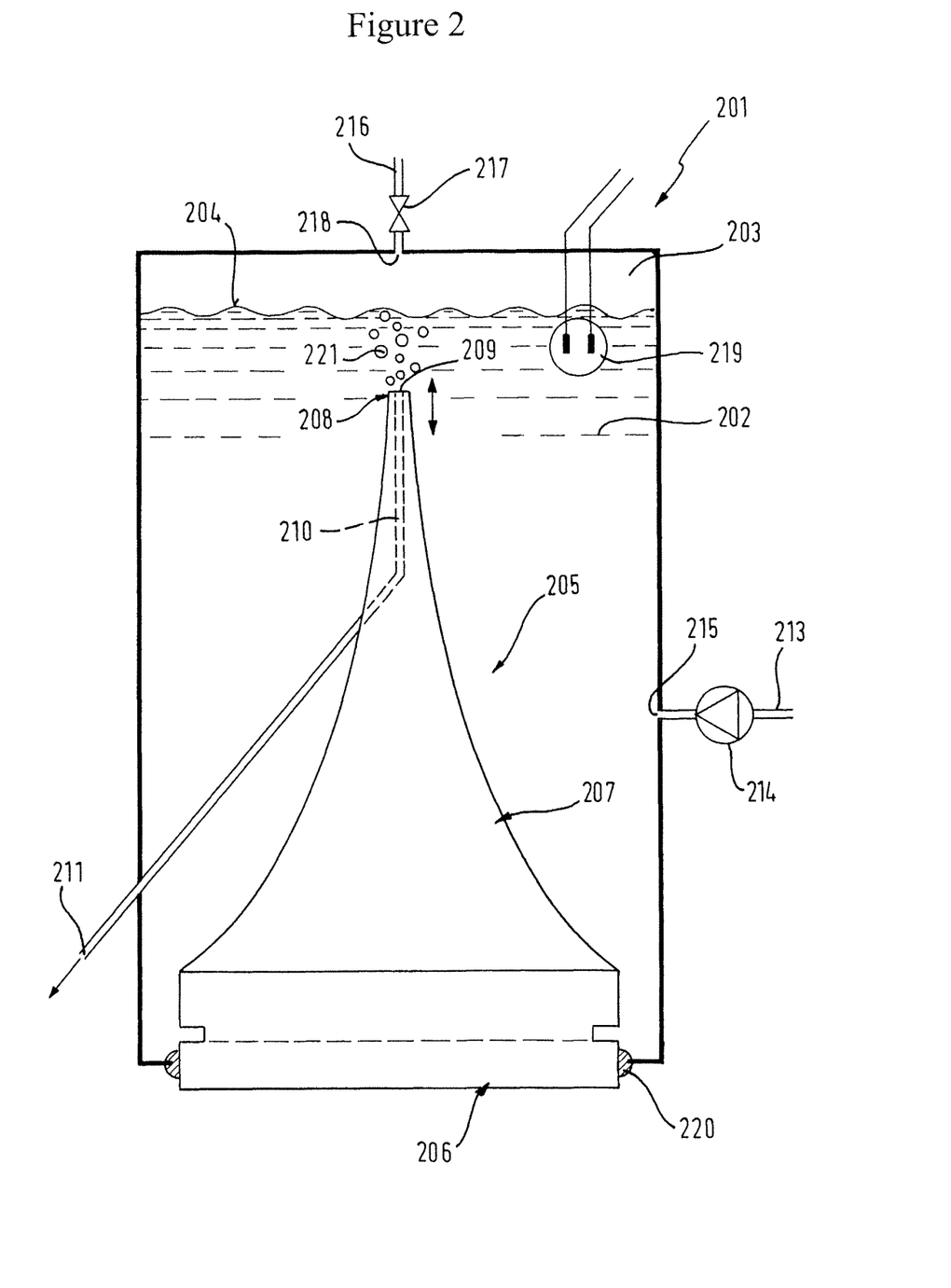
FIG. 2 depicts a degassing unit according to another embodiment of the invention.

FIG. 2 shows essentially the same features as in FIG. 1 but in a different arrangement. The reference numerals correspond largely to those from FIG. 2, but for a better correspondence, the reference numerals according to FIG. 2 are numbered continuously starting from the number 200. In contrast with FIG. 2, the arrangement of the resonator 207 and the oscillator 206 inside the degassing unit 201 is reversed. In the embodiment shown here, the resonator 207 is completely surrounded by the liquid 202 to be degassed. The tip 208 of the resonator 207 is next to the gas/liquid interface 204 but is inside the liquid space 202.

In contrast with the embodiment according to FIG. 1, the oscillator 206 is arranged with a seal by means of the gaskets 220 in the wall of the degassing unit 201. Gas can be discharged from the degassing unit through the opening 218 of the degassing unit and through a channel 216 by means of a cutoff valve 217. By controlling the cutoff valve, the gas pressure can be regulated by means of the liquid volume, which thus also makes it possible to regulate the flow rate at which the mixture of degassed liquid and gas is discharged from the degassing unit through the discharge channel 210, 211. The volume and pressure of the gas space 203 are influenced by gas bubbles 221, which are already separating, and by liquid flowing in through the channel 213.

For example, a level sensor 219 is shown; this makes it possible to check on whether or not the liquid level has been set too low for the position of the resonator tip 208. The level sensor may consist of simple electrodes with the help of which it is possible to make inferences about the liquid level, e.g., by measuring the electrical resistance, the impedance or the electrical conductivity.

Figure 3:
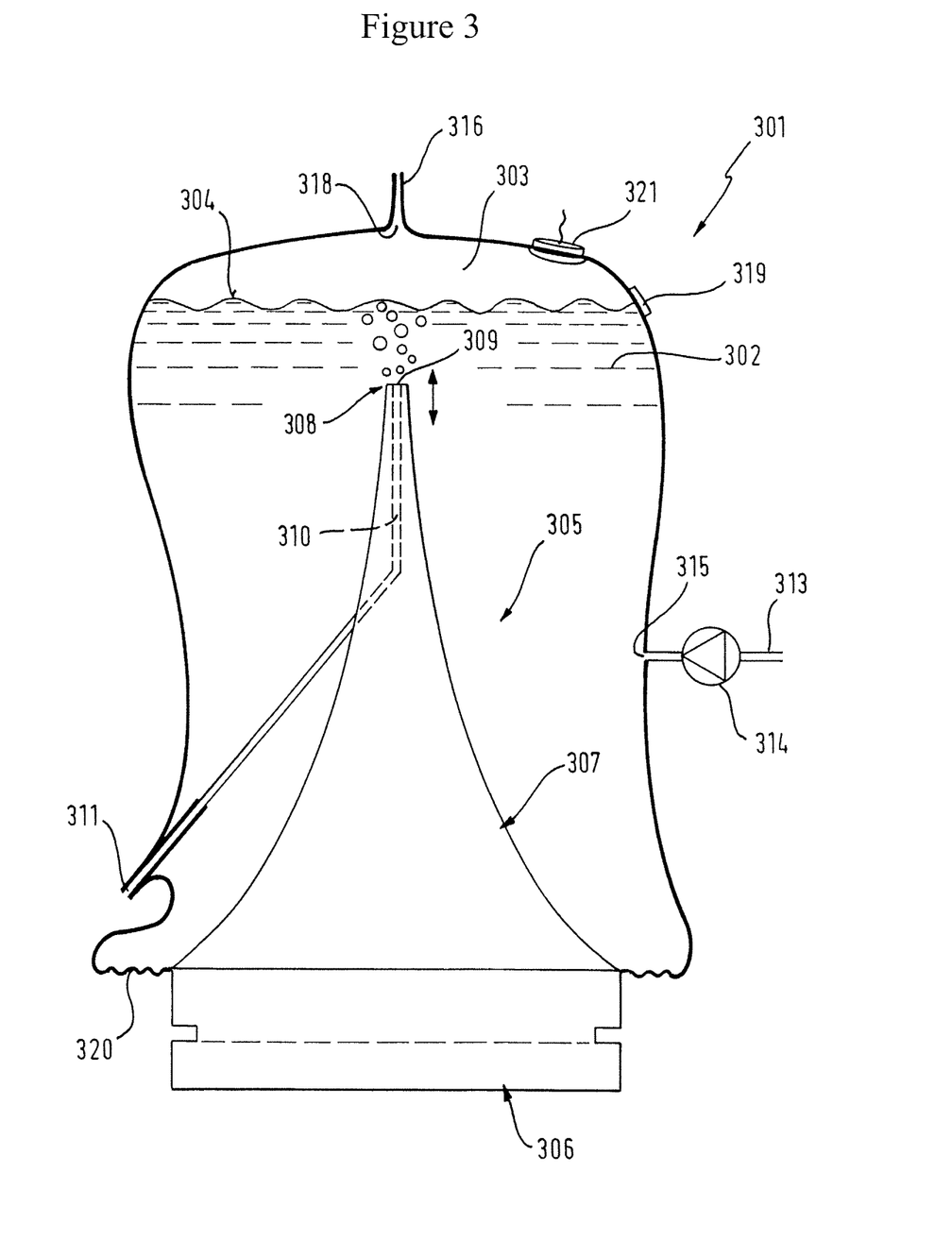
FIG. 3 depicts a degassing unit according to still another embodiment of the invention.

FIG. 3 shows an alternative embodiment in comparison with the embodiments shown in FIGS. 1 and 2. This shows the arrangement of an external oscillator and a degassing unit 301 with a resonator, where the figure shows the degassing unit 301 in a cutout of a disposable article. The reference numerals correspond largely to the reference numerals used in FIGS. 1 and 2, but for a better correspondence, the reference numerals according to FIG. 3 have been numbered continuously from the number 300.

FIG. 3 shows the resonator 307 arranged inside the degassing unit 301 of a disposable article. The resonator, as in the embodiment according to FIG. 2, is surrounded here by liquid to be degassed. The tip 308 of the resonator 307 is located in proximity to the gas/liquid interface 304 within the liquid volume 302. The degassing unit is bordered on one side by the membrane 320, which is connected to the degassing unit with a seal. The membrane is a flexible wall which may also be embodied as a film. A rubbery membrane, e.g., made of a mixture of materials from the group of materials comprising styrene block copolymers, polypropylenes, polyethylenes, poly-α-olefins, their polymers and blends, is advantageous. In addition, a material that is vibration-resistant under the vibration conditions of the oscillator should be selected in particular.

The oscillator 306 is arranged next to the membrane 320 and transmits the oscillation energy to the resonator 307 via the membrane 320. The oscillator 306 is arranged externally to the disposable article with the degassing unit 301. The oscillator is preferably arranged in the console of a treatment machine, which is not shown in FIG. 3.

As an alternative to the embodiment according to FIG. 2, the degassing unit according to FIG. 3 is equipped with a level sensor 319 to be able to determine the liquid level 304.

The sensor does not enter the liquid. Corresponding sensors are known in the state of the art, e.g., magnetoresistive sensors or ultrasonic sensors.

In addition, a pressure sensor 321, which can measure the gas pressure of the gas space 303, may be arranged on the degassing unit 301 according to FIG. 3. If the pressure is too high, gas can be discharged from the chamber through the channel 316. All the incoming and outgoing channels 318, 311, 313 can be equipped with valves, which are not shown in the figure, to be able to control fluids flowing in and flowing out.

The following list shows the reference numerals, which are used in FIGS. 1, 2 and 3, along with the explanation thereof and their correspondences:

| | |
|---|---|
| Container and degassing unit | (1), (201), (301) |
| Liquid space/liquid to be degassed | (2), (202), (302) |
| Gas space | (3), (203), (303) |
| Liquid gas/interface | (4), (204), (304) |
| Ultrasonic unit | (5), (205), (305) |
| Oscillator | (6), (206), (306) |
| Resonator | (7), (207), (307) |
| Resonator tip | (8), (208), (308) |
| Opening in the resonator tip | (9), (209), (309) |
| Hollow channel | (10), (210), (310) |
| Opening for discharge of degassed liquid | (11), (211), (311) |
| Liquid supply channel | (13), (213), (313) |
| Feed pump | (14), (214), (314) |
| Feed opening | (15), (215), (315) |
| Inlet/outlet channel for gas/air | (16), (216), (316) |
| Gas supply/discharge pump | (17) |
| Gas valve | (217) |
| Gas supply/discharge opening | (18), (218), (318) |
| Liquid level sensor | (219) |
| Level sensor | (319) |
| Housing gasket | (220) |
| Wall membrane | (320) |
| Separated gas bubbles | (221) |
| Pressure sensor | (321) |

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A device for degassing a liquid for dialysis or for an extracorporeal blood treatment, said device comprising:
    a container of a degassing unit to receive the liquid; and
    a resonator, which is configured for immersion in the liquid of the container, and which induces a degassing of the liquid through ultrasound,
    with the resonator including a hollow channel via which the degassed liquid is discharged from the container.
2. The device according to claim 1, wherein
    the resonator has an elongated extent configured at an end thereof as a tip.
3. The device according to claim 1, wherein
    a surface of the resonator has a hyperbolic curvature.
4. The device according to claim 1, further comprising
    a pump, to which the degassing unit is connected, with the pump being configured to create an excess pressure in the container.
5. The device according to claim 1, further comprising
    a second container connected to an outgoing end of the hollow channel to receive the degassed liquid.
6. The device according to claim 1, further comprising
    an oscillator, to which the resonator is connected, with the oscillator being configured as a float.
7. The device according to claim 1,
    wherein the resonator is completely immersed in the liquid to be degassed.
8. The device according to claim 2,
    wherein the tip of the resonator is below a liquid/gas interface on a liquid side thereof.
9. The device according to claim 1, further comprising
    a processor to which at least one of the oscillator and the resonator is connected, with the processor being configured to determine a control value based on a damping value that has been determined, and to vary an oscillation frequency of the oscillator so that the damping is minimized.
10. An assembly of an ultrasonic oscillator and a disposable article with a device according to claim 1,
    wherein the resonator is integrated into the disposable article, and the oscillator is integrated into a console of a treatment machine separately from the resonator, and
    wherein the disposable article and the machine console are brought into engagement with one another such that the oscillator is arranged on the disposable article so as to transmit vibrations to the resonator.
11. A disposable article having a device for degassing a liquid according to claim 1.
12. A method of degassing a liquid for dialysis or extracorporeal blood treatment, said method comprising the following steps:
    introducing a liquid into a container of a degassing unit;
    immersing a resonator into the liquid to be degassed, and degassing the liquid by ultrasonic treatment;
    discharging at least one of the liquid and the separated gas through a hollow channel in the resonator.
13. The method according to claim 12,
    wherein the discharging step includes discharging the liquid and the separated gas together through the hollow channel, and collecting the liquid and the separated gas in a second container.
14. The method according to claim 13,
    further comprising a step of separating the collected liquid and separated gas in the second container.
15. The method according to claim 13,
    further comprising a step of selectively removing the degassed liquid from the second container for further processing.

* * * * *